(12) United States Patent
Gruber et al.

(10) Patent No.: US 8,889,184 B2
(45) Date of Patent: Nov. 18, 2014

(54) PARTICULATE FORM OF A PHARMACEUTICAL COMPOSITION WHICH IS EASY TO SWALLOW

(75) Inventors: Peter Gruber, Merzhausen (DE); Peter Kraahs, München (DE)

(73) Assignee: Losan Pharma GmbH, Neuenburg (DE)

( * ) Notice: Subject to any disclaimer, the term of this patent is extended or adjusted under 35 U.S.C. 154(b) by 1675 days.

(21) Appl. No.: 11/516,573

(22) Filed: Sep. 7, 2006

(65) Prior Publication Data

US 2008/0063713 A1 Mar. 13, 2008

(51) Int. Cl.
*A61K 9/46* (2006.01)
*A61K 9/50* (2006.01)

(52) U.S. Cl.
CPC .................. *A61K 9/5042* (2013.01)
USPC ............ 424/466; 424/464; 424/465; 424/474

(58) Field of Classification Search
USPC .................. 424/464, 465, 466, 477
See application file for complete search history.

(56) References Cited

U.S. PATENT DOCUMENTS

| | | | | |
|---|---|---|---|---|
| 2,011,587 A | * | 8/1935 | Miller | 424/476 |
| 3,324,002 A | * | 6/1967 | Antonides | 424/94.2 |
| 3,506,756 A | * | 4/1970 | Hoss | 424/44 |
| 4,882,169 A | | 11/1989 | Ventouras | |
| 5,288,500 A | | 2/1994 | Ibsen | |
| 5,587,180 A | * | 12/1996 | Allen et al. | 424/499 |
| 5,651,985 A | * | 7/1997 | Penners et al. | 424/469 |
| 5,733,575 A | * | 3/1998 | Mehra et al. | 424/480 |
| 5,807,580 A | * | 9/1998 | Luber | 424/480 |
| 5,840,332 A | * | 11/1998 | Lerner et al. | 424/464 |
| 6,156,339 A | * | 12/2000 | Grother et al. | 424/450 |
| 6,228,398 B1 | * | 5/2001 | Devane et al. | 424/484 |
| 6,667,056 B2 | * | 12/2003 | Chiesi et al. | 424/466 |
| 2004/0247675 A1 | | 12/2004 | Gruber | |

FOREIGN PATENT DOCUMENTS

| | | | |
|---|---|---|---|
| EP | 0040590 A2 | * | 11/1981 |
| WO | WO 97/42941 | | 11/1997 |
| WO | WO-00/56266 | * | 9/2000 |
| WO | WO 2005/105036 | | 11/2005 |

OTHER PUBLICATIONS

Chun et al., Preparation and Characterization of Enrofloxacin/Carbopol Complex in Aqueous Solution, 2004, Archives of Pharmaceutical Research, vol. 27 No. 6, pp. 670-675.*

* cited by examiner

*Primary Examiner* — Ali Soroush
(74) *Attorney, Agent, or Firm* — Smith Patent; Chalin A. Smith

(57) ABSTRACT

The present invention relates to a pharmaceutical composition for direct oral administration which is very easy to swallow especially for young children, comprising at least one pharmaceutically active compound. The pharmaceutical composition is present in the form of one or more particles. The particles comprise a core containing the active ingredient which has been provided with one or more coatings. The pharmaceutical composition is preferably administered in combination with a powder and/or granules which, when applied to the tongue, spontaneously generate additional saliva. With the extra saliva, the coated particles form a soft, smooth, but mechanically stable surface perceived as pleasant in the mouth within seconds so that they may be swallowed easily and practically in the right quantity with the extra saliva formed.

19 Claims, 1 Drawing Sheet

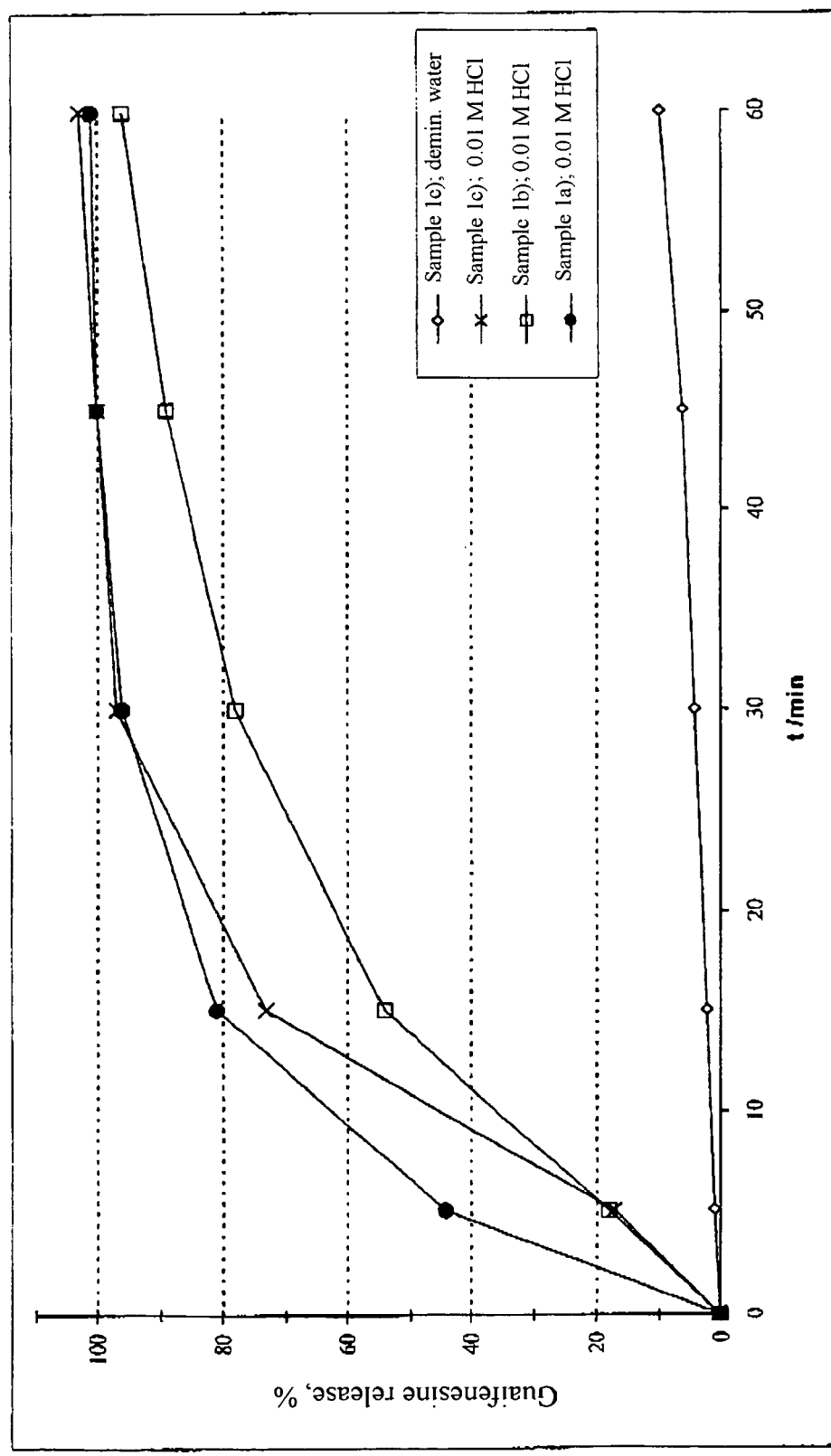

PARTICULATE FORM OF A PHARMACEUTICAL COMPOSITION WHICH IS EASY TO SWALLOW

FIELD OF THE INVENTION

The present invention relates to a pharmaceutical composition for direct oral administration which is very easy to swallow especially for young children and which comprises at least one pharmaceutically active compound. The pharmaceutical composition is present in the form of one or more particles. The particles consist of a core containing the active ingredient which has been provided with one or more coatings. The pharmaceutical composition is preferably administered in combination with a powder and/or granules which, when applied to the tongue, spontaneously generate saliva. Within seconds, the coated particles form a soft, smooth, but mechanically stable surface with the saliva, which is perceived as pleasant in the mouth so that they may be swallowed easily and practically in the right quantity.

BACKGROUND OF THE INVENTION

The oral ingestion of solid medicament forms (especially of tablets and capsules) is accompanied by numerous problems for children and older people. Children must be 6 to 8 years old before they can reliably swallow solid medicament forms, there being major restrictions concerning the size of the medicament forms. Older people often suffer from swallowing disorders, too, which are caused by a decrease in saliva formation in old age so that the solid medicament forms may be swallowed only with difficulty. They react with reluctance to the regular ingestion often necessary over many years which frequently leads to irregular compliance.

In an attempt to solve these problems, numerous alternatives have been offered in the market place. However, tablets for chewing or sucking and orodispersible tablets are not a genuine alternative either, especially for young children. Due to dental problems, older people often have an aversion against chewable tablets, too, and sucking tablets or orodispersible tablets are not convincing either due to reduced salivation. In addition, an expensive and complicated step is necessary to first convert the active ingredients which often have a bitter taste into small saliva-resistant particles before they are processed into chewable tablets, sucking tablets or orodispersible tablets, the masking of the taste often being more or less destroyed by the subsequent necessary compression to tablets with the result that the bitter taste often leads to an aversion against this medicament form. The processing of release-controlled enteric-coated or retarded particles into the above medicament forms is even more problematic. Again, the subsequent compaction causes at least partial destruction of the coating layer. As a result, formulators attempt to protect the saliva-resistant particles by a large amount of adjuvants which are easily compressed. This, in turn, raises the cost of preparing these tablets and increases the tablet size unnecessarily.

Therefore, there are granules and powders on the market which usually must be converted into a suspension with a certain amount of water before ingestion. In most cases, such suspensions require preservation, must be kept in the refrigerator and generally entail high production costs. Often mistakes are made when the suspension is prepared. By foaming or insufficient agitation before application, problematic dosing errors may occur, and especially older people have problems with this dosage form.

With young children or adults with swallowing disorders, a syrup is often chosen as an alternative. In many cases, however, problems occur because the active ingredient is very bitter. Syrups must always be protected by preservatives which have an inherent allergy risk. In many active ingredients, stability problems occur when they are processed into an aqueous syrup.

U.S. Pat. No. 4,882,169 proposes coated pellets having a diameter of 0.2 to 3 mm which allegedly form a homogeneous dispersion in water. The particles contain at least one pharmaceutically active substance, optionally one or more release-controlling or taste-masking coatings and one swellable outer layer. The latter contains a swellable polymer, preferably guar, and a binder. Together with guar granules and flavouring agents, the coated pellets are bagged into sachets from which they are taken and dispersed in water.

U.S. Pat. No. 5,288,500 proposes to combine a plurality of particles containing the active ingredient having a diameter of 0.05 to 7 mm with a gelling or swelling agent. The latter may be present in admixture with the particles containing the active ingredient, be contained on a coating, be added to the particles containing the active ingredient before admixing with an aqueous carrier or be dispersed in an aqueous carrier to which the particles containing the active ingredient are admixed. The proposed formulation is dispersed in an aqueous carrier. In particular, hydrophilic polymers forming colloidal dispersions, sols or suspensions in an aqueous environment are indicated as gelling or swelling agents for the formulations proposed in U.S. Pat. No. 5,288,500. The polymers are used in an amount sufficient to ensure that dispersal in an aqueous carrier is not impaired. If desired, the viscosity in the immediate vicinity of the dispersed particles may be influenced by the formation of salt, chelation, changes of polarity and such like. The components of the formulation may be kept separate until they are processed or bagged into sachets or processed to tablets or capsules.

The formulations described in U.S. Pat. No. 4,882,169 and U.S. Pat. No. 5,228,500 are ingested together with an aqueous carrier wherein they must be dispersed before administration. In this process, the formulations disintegrate into individual particles so that quantitative ingestion is not guaranteed as a rule. This is because, in general, drinking a particle suspension or dispersion is a real problem, for after the solution has been drunk a residue of the particles is usually left on the bottom of the vessel and can be brought into the mouth with difficulty only. It is not at all sure either whether the patient will even try to do this. Sedimentation of the particles may be prevented partially only by drinking the particle suspension very quickly after stirring. Such a medicament form which requires fast drinking is particularly unsuitable for young children and older patients.

Formulations according to the two cited patents have the disadvantage that quantitative ingestion in the prescribed dose is generally not guaranteed and that they must be pre-dispersed in an aqueous carrier first, i.e. clean drinking water and a suitable vessel must be available which renders ingestion difficult, especially when travelling.

An improved agent is disclosed in WO 98/06385. The printed publication describes a pharmaceutical composition in the form of particles which may be ingested directly even without liquid. The pharmaceutical composition is for oral administration and contains one or more coated active ingredient particles having a coating consisting of one or more layers, the composition of the coating being characterised in that a) the coating layer or coating layers contain at least one hydratable polymer which, upon contact with saliva or water, forms a continuous, mouldable, viscous sticky particle mass which prevents particles containing the active ingredient from escaping from this mass and the release of the active ingredient in the oral cavity, and b) the outer coating layer contains an effective amount of at least one agent which promotes salivation.

It is the disadvantage of that invention that it is difficult for young children and older people to keep the particles poured onto the tongue together until saliva combines the individual particles into a particle mass. Especially children will distribute the polymer-coated particles in the mouth and the saliva formed is insufficient for the particles sticking to the surface to be swallowed without the aid of water. Since the particles poured into the mouth often do not or not sufficiently stick together in a particle mass, the release of the active ingredient from the particles is increased so that there is only insufficient protection against the unpleasant bitter taste of the active ingredient. This active ingredient may diffuse much more easily from individual particles than from a sticky lump of particles with a much reduced surface releasing the active ingredient. It is the objective of this development of the prior art to generate only that amount of saliva sufficient to make the polymers sticky on the surface so that they form a lump. It is not an objective of the development to cause major spontaneous salivation immediately after ingestion which would facilitate swallowing tasteprotected particles. Only if the particles poured onto the middle of the tongue are skilfully pressed against the palate for approx. 30 to 60 seconds will they agglutinate, forming a continuous, mouldable, viscous particle paste which may be swallowed with comparative ease. Also, it has been shown that a practically quantitative agglutination of the individual particles is never achieved and individual particles diffuse into the oral cavity, for instance between the teeth, which is a disadvantage.

Especially with children, it is of particular importance that a mechanically stable, soft particle surface is quickly formed upon contact with saliva which cannot be removed by tongue movement and gives the particles a pleasant feel in the mouth. In general, hard granules, coarser crystals, but also pellets are perceived as unpleasant foreign bodies in the mouth because of their rough surface. Especially with young children, this will lead to a refusal to ingest or swallow these particles, or the children will try to spit them out. Therefore, it is important that a soft, but mechanically stable surface is formed on these particles within seconds after ingestion. Especially for children, it is difficult to swallow the particles containing the active ingredient quickly and in the right quantity. Rather, they will tend to distribute the particles through the entire oral cavity. In addition, uncontrolled tongue movements will exert a strong mechanical stress on the particle surface so that a swollen, unfixed polymer present on the surface is easily rubbed off and the rough particle surface which is perceived as unpleasant re-emerges.

To ensure that especially young children will swallow a pharmaceutical composition in particulate form without undue persuasion, it is important that these particles do not cause a sandy, hard, grainy, unpleasant feeling in the mouth, but have a mechanically stable, soft, non-sticky surface which forms very quickly.

SUMMARY OF THE INVENTION

It is therefore an object of the invention to provide a pharmaceutical composition which does not display any of the above problems. The pharmaceutical composition should also be suitable for easy ingestion by young children and older people in the right quantity without any unpleasant feeling (in the mouth) occurring during ingestion. In a preferred embodiment, the pharmaceutical composition should be easily ingestible without water.

This object is achieved by the subject matter of the claims. Therefore, the present invention provides a pharmaceutical composition for oral administration in the form of at least one particle containing an active ingredient comprising a) a core which contains the active ingredient of the particle and, optionally, suitable adjuvants, and b) one or more coating layers applied to the core, the one coating layer or the outermost coating layer of the more coating layers containing (i) at least one polymer capable of forming a gel with water, (ii) at least one polymer not capable of forming a gel with water, (iii) at least one compound capable of releasing carbon dioxide, and (iv) optionally, additional adjuvants.

In a preferred embodiment, the pharmaceutical composition of the invention is present in combination with one or more compounds promoting salivation. This embodiment is especially preferred if the pharmaceutical composition is to be administered without a carrier such as water or other food.

These and other objects, features, benefits and advantages of the present invention will become more fully apparent when the following detailed description is read in conjunction with the accompanying examples, figures, data, and all reasonable inferences to be drawn therefrom.

BRIEF DESCRIPTION OF THE DRAWINGS

FIG. 1 depicts the results of a dissolution test carried out in artificial gastric juice according to the U.S. Pharmacopoeia, paddle method, 50 rpm, depicting the release values of guaifenesine pellets 1a), pellets 1b) not coated according to the invention and pellets 1c) according to the invention.

DETAILED DESCRIPTION OF THE PREFERRED EMBODIMENTS

The invention is based on the surprising finding that a fast-forming, mechanically stable and yet soft, but not sticky surface may be achieved for active ingredient particles if the active ingredient particles are provided with a coating wherein a saliva-resistant polymer, i.e. a polymer which is insoluble in saliva (or water, respectively) and is not capable of forming a gel with saliva (or water, respectively) is combined with a polymer which is capable of forming a gel with saliva (or water, respectively) and therefore swells fast and if carbon dioxide is generated in the coating upon contact with saliva or water. Without wishing to be bound by theory, the Applicants assume that the carbon dioxide is created in the form of carbon dioxide micro-bubbles which "blow up" the coating and thus generate the advantageous surface.

A polymer capable of forming a gel with water (gel-forming polymer) is understood to mean a polymer which forms a gel in water in a 2 wt.-% solution or colloidal dispersion at a pH of 7.0. A polymer not capable of forming a gel with water (non-gel-forming polymer) is understood to mean a polymer which does not form a gel and is insoluble in water at a pH of 7.0.

Regarding the definition of a gel, reference is made to the standard work Römpp, Lexikon der Chemie, 10$^{th}$ ed, Thieme Verlag, Stuttgart. If necessary, the pH value of 7.0 is adjusted by the addition of an acid such as HCl (with alkaline polymers) or a base such as NaOH (with acidic polymers).

According to the invention, a gel-forming or non-gel-forming polymer may alternatively be defined by the viscosity. Accordingly, a gel-forming polymer is a polymer which has a viscosity of at least 1000 mPa·s, preferably at least 2000 mPa·s, more preferably at least 5000 mPa·s and especially at least 10,000 mPa·s in a 2% (wt./wt.) aqueous dispersion or solution at a pH value of 7.0. If necessary, the adjustment of the pH value to pH 7.0 is done as described above with an acid or a base.

Accordingly, a non-gel-forming polymer is a polymer which has a viscosity of not more than 200 mPa·s, preferably not more than 100 mPa·s and especially not more than 50 mPa·s, most preferably of not more than 20 mPa·s in a 2% (wt./wt.) aqueous dispersion at a pH value of 7.0. If necessary, adjustment of the pH value to pH 7.0 is done as described above with an acid or a base.

In the invention, a gel-forming polymer is especially understood to mean those polymers which are expressly mentioned as gel-forming polymers or as component b) (i); a non-gel-forming polymer according to the invention is especially understood to mean those polymers which are expressly mentioned as non-gel-forming polymers or as component b) (ii).

The extent of gel-formation may be determined by measuring the viscosity. Unless otherwise indicated or obvious, the following observations apply to all viscosity values indicated in this application.

For a number of polymers, rules for determining the viscosity are described in Ph. Eur., 5$^{th}$ ed., a standard work 2005. For these polymers, the viscosity is determined as prescribed there, but in a 2% solution or dispersion at a pH value of 7.0.

If no rule concerning the determination of the viscosity is given in Ph. Eur., 5$^{th}$ ed., standard work 2005, or if the rule is not sufficiently clear or practicable, the viscosity is determined as follows:

An amount corresponding to 2.00 g of the dried substance is suspended in 50 g of water R with stirring. The suspension is diluted with water R and, in order to adjust the pH value to 7.0, optionally with a suitable base (such as NaOH) or a suitable acid (such as HCl) to 100.0 g and stirred, until the substance is completely dispersed or dissolved. The viscosity is determined at 25° C. with the aid of a rotation viscosimeter and a shear gradient of 100 s$^{-1}$ for substances with an expected viscosity of not more than 100 mPa·s, a shear gradient of 10 s$^{-1}$ for substances with an expected viscosity of between 100 and 20,000 mPa·s, and a shear gradient of 1 s$^{-1}$ for substances having an expected viscosity of more than 20,000 mPa·s. If the prescribed shear gradient cannot be complied with exactly, a somewhat higher or lower shear gradient is used and then interpolated.

If the viscosity cannot be determined by this method, the following method is used.

In a 500 ml beaker, 6.0 g of the substance are added to 250 ml of a solution of potassium chloride R (12 g/l) with stirring in a slightly inclined propeller agitator operated at a rotational speed of 800 rpm over 45 to 90 sec. and, if necessary, the pH value adjusted to 7.0 with a suitable base (such as NaOH) or a suitable acid (such as HCl). When the substances are added, no aggregates must remain. Residues adhering to the wall of the beaker are rinsed off with additional water R so that a weight of 300 g results. The composition is stirred at a temperature of 25° C. with a rotational speed of 800 rpm for 2 hours. This viscosity must then be determined within 15 min, using a rotation viscosimeter running a 60 rpm. This viscosimeter is equipped with a rotational spindle having a diameter of 12.7 mm and a height of 1.6 mm. Said rotational spindle is mounted on a shaft having a diameter of 3.2 mm. The spacing from the upper part of the cylinder to the bottom of the shaft is 25.4 mm, the immersion depth 50.0 mm.

This rule is similar to the rule in Ph. Eur., 5$^{th}$ ed., standard work 2005, for xanthan gum.

Unless expressly disclosed otherwise or evident to a skilled practitioner, a pH value is determined at 25° C. in a 3% aqueous dispersion or solution.

Unless expressly disclosed otherwise or evident to a skilled practitioner, parts and ratios are always based on the weight.

The pharmaceutical composition for oral administration is present in the form of at least one particle containing the active ingredient. As a rule, however, the pharmaceutical composition is composed of several particles containing the active ingredient. The size of the particles containing the active ingredient constituting the pharmaceutical composition for oral administration is not particularly limited. If the pharmaceutical composition of the invention is a single particle (e.g. a tablet), the particle may have a size of up to about 15 mm, preferably up to about 10 mm. So-called oblong tablets having a length of up to 25 mm, a thickness of up to 10 mm and a width of up 12 mm are also possible. If the pharmaceutical composition is composed of several particles, the size of the particles is generally in a range of 0.05 to about 7 mm, preferably 0.1 to 5 mm, more preferably 0.2 to 3 mm.

A particle of the invention containing the active ingredient comprises a core and one or more coatings. Usually, the active ingredient is contained only in the core of the particles containing the active ingredient. Suitable cores containing the active ingredient are, for example, screened granules prepared in the classical way and having a grain size of 0.05 to 1.0 mm with a rough surface or sharp-edged active ingredient crystals having a grain size range of 0.05 go 2.0 mm. It goes without saying, that pellets prepared from so-called non-pareilles by the application of the active ingredient(s), especially those with a rough surface, as well as pellets prepared by the known method of extrusion and spheronisation of a workable mass containing the active ingredient also constitute suitable cores containing the active ingredient. Finally, this invention is particularly well suited for mini-tablets of 1.5 to 3.5 mm, since these may have sharp edges as a result of compaction that are perceived as particularly unpleasant when swallowed.

The composition of the invention is generally suitable for the administration of any therapeutically and/or prophylactically effective oral-administration active ingredients (phyto extracts, minerals, trace elements, vitamins, vital substances), such substances being present in the cores, i.e. as granules, pellets or micro-tablets of a size of 0.05 to 3.5 mm (before coating).

The active ingredients are, for example, gastro-intestinal agents and agents promoting digestion such as loperamide, metoclopramide, pancreatin, amylase, protease, lipase or sulfasalazine, olsalazine and mesalazine and cimetidine, ranitidine, famotidine, nizatidine and proton pump inhibitors such as omeprazol, pantoprazol, lansoprazol, as well as laxatives such as bisacodyl, sodium picosulfate.

Suitable active ingredients are particularly analgesics and anti-rheumatic agents such as acetyl salicylic acid, paracetamol, ibuprofen and its water-soluble salts of sodium, potassium and lysine, tramadol, acemetacine, naproxene, naproxene-sodium, diclofenac, ketoprofen, piroxicam, indometacine as well as anti-allergy agents such as astemizol, ketotifen, cetirizine, loratadine and fexofenadine, β-receptor blockers, calcium antagonists and ACE inhibitors, coronary medicaments, anti-Parkinson agents and sedatives such as nitrazepam, oxazepam, docusate-sodium, and zolpidem. Additional suitable active ingredients are antibiotics such as ciprofloxacine, norfloxacine, ofloxacine, nalidixinic acid, cinoxacine, pefloxacine, phenoxy methyl penicillin, amoxicillin and other penicillins having a penam structure, cephalosporins having a cephem structure such as cefaclor, cefadroxil, cefalexine, cefpodoxim, ceftibuten, cefuroxim and cefetamet, clavulanic acid in combination with amoxicillin, tetracycline, macrolide antibiotics such as erythromycin and its esters, spiramycin and josamycin, collistin and polymycin B, nitrofuranes such as nitrofurantoin, nitroimidazoles such as metronidazole and active ingredients such as clarithromycin, azithromycin, griseofulvin and sulfamethoxazole in combination with trimethoprim. The composition of the invention is also suitable for the administration of mineral salts of calcium, magnesium, zinc, iron and of trace elements such as chromium, manganese, selenium etc., and especially of all vitamins. If desired, the composition may contain combinations of vitamins and/or minerals and/or trace elements with/without vital substances (carnitin, soy isoflavones, phytosteroles). Particularly suitable are active ingredients used in paediatrics such as the anti-cough agents and expectorants guaifenesine, ambroxol, bromhexine, acetyl cysteine, codeine, theophyline and, for example, combinations of guaifenesine with dextromethorphan-hydrobromide, phenylephrine-HCl and diphenylhydramine-HCl. The particles of the invention containing the active ingredient may, for example, contain the guaifenesine in combination with phenylephrine or dextromethorphan-HBr. Alternatively, the active ingredient particles of guaifenesine and dextromethorphan or phenylephrine made according to the invention may be mixed with each other and, optionally, with the saliva-forming component. Also preferred are preparations containing steroids such as prednisolone and salts thereof as the active ingredient.

In general, active ingredients are particularly suitable which have an unpleasant and/or bitter taste such as guaifenesine, prednisolone, codeine and caffeine as well as active ingredients having a high dosage amount and, optionally, an unpleasant taste as well such as 5-amino salicylic acid (individual dose up to 1.5 g), gabapentine (individual dose up to 1.5 g), ibuprofen and its water-soluble salts (individual dose up to 800 mg of ibuprofen) and paracetamol (individual dose up to 1.0 g). However, combinations of paracetamol and/or acetyl salicylic acid and/or caffeine and/or vitamin C are suitable combinations of active ingredients. According to the invention, the active ingredient guaifenesine, the active ingredient dextromethorphan (or a salt thereof), a mixture of guaifenesine and dextromethorphan (or a salt thereof) a mixture of guaifenesine and phenylephrine (or a salt thereof) or prednisolone are particularly preferred. Optionally, prednisolone may be present in the form of an ester such as prednisolone acetate, prednisolone phosphate-Na or prednisolone sulfate-Na.

When an active ingredient is mentioned in this application, this may be an individual active ingredient or a mixture of several active ingredients.

In addition to the active ingredient, the core of the pharmaceutical composition of the invention may contain the customary pharmaceutical adjuvants known to a skilled practitioner, especially the adjuvants usually used for preparing granular pellets or micro-tablets. For the preparation of the particles of the invention which contain the active ingredient, reference may be made to the customary standard literature on pharmaceutical technology, such as "W. A. Ritschel, A. Bauer-Brandl, Die Tablette, publishers Editio-Cantor, 2002".

It is essential for the invention that the core of the pharmaceutical composition of the invention has one or more coatings. In the event that several coatings are present, these are usually placed on top of each other, and the outermost of these coatings is particularly important in the invention. This outermost coating or, in the event that only one coating is used, this one coating is designated "coating according to the invention" in the following.

The coating according to the invention contains at least three components which are different from each other. One of the components (component b)(i)) is a polymer capable of forming a gel with water. This polymer swells as a result of the rapid uptake of water or saliva. The second component (component b)(ii)) is a polymer which does not form a gel with water and therefore practically does not swell when in contact with water of saliva. It is substantially insoluble at a pH of 7.0, i.e. it is insoluble also in saliva. This polymer not capable of forming a gel with water may be soluble or insoluble in gastric juice. Preferably, it is a polymer which is soluble or forms a dispersion in water at a pH of 5 or less, preferably of 3.5 or less (and thus also in gastric juice). If this polymer forms a dispersion at pH of 5 or less, preferably of 3.5 or less, this dispersion has a viscosity of 100 mPa·s or less, preferably 50 mPa·s or less, especially 10 mPa·s or less (2% wt./wt. dispersion).

The third substantial component (component b)(iii)) of the coating of the invention is a compound capable of releasing carbon dioxide. In accordance with the invention, such a compound or several such compounds may be present in the coating according to the invention. Especially preferably, these compounds capable of releasing carbon dioxide are inorganic carbonates or hydrogen carbonates; carbonates and hydrogen carbonates of alkali metals and alkaline earth metals, i.e. compounds of the formula $MH_n(CO_3)$ wherein M is an alkali or alkaline earth metal ion and n=0 or 1, n being 0 when M is an alkaline earth metal ion. Sodium hydrogen carbonate, potassium hydrogen carbonate, calcium carbonate, magnesium carbonate and mixtures of these compounds are most preferred. Sodium glycin carbonate is also preferred according to the invention. Most preferred for the invention are the hydrogen carbonates sodium hydrogen carbonate and potassium hydrogen carbonate and mixtures thereof.

In another embodiment, the coating according to the invention may contain alkaline adjuvants such as trisodium citrate, trisodium/tripotassium citrate or trisodium phosphate in addition to the alkaline carbon dioxide-releasing compounds. The carbon dioxide-releasing compounds, especially the hydrogen carbonates/carbonates, sodium/potassium hydrogen carbonate, sodium/potassium carbonate, calcium carbonate, magnesium carbonate, sodium glycin carbonate and optionally the other alkaline adjuvants that may additionally be employed, are preferably used in micronised form when preparing the coating according to the invention. The mean particle size is preferably 0.1 mm maximum, most preferably 5 to 50 μm maximum.

The inorganic carbonates or hydrogen carbonates release carbon dioxide particularly when they come into contact with acidic compounds and water. In addition to the compound capable of releasing carbon dioxide, the coating according to the invention therefore preferably contains a compound which, when in contact with water or saliva, provides an acid which promotes or effects the release of the carbon dioxide. In accordance with the invention, the polymer forming a gel with water or the polymer not forming a gel with water may be an acidic polymer. It is also possible that both polymers are acidic polymers. In accordance with the invention, an "acidic polymer" is understood to mean a polymer which provides a pH of <7 in an aqueous solution or dispersion; preferably it is understood to mean a polymer which provides a pH value of ≤6, more preferably ≤5 in a 3% solution or dispersion in water.

It is also preferred for the invention that an acidic compound as described below is added to the coating according to the invention. As soon as the coating according to the invention therefore comes in contact with water or saliva in the mouth, carbon dioxide micro-bubbles form in the coating according to the invention which, together with the other components of the coating according to the invention, ensure that a soft particle surface which is perceived as pleasant in the mouth, but which is mechanically stable is formed within seconds.

Polymers which are capable to form a gel with water (component b)(i)) are well known. If water or saliva is provided to these polymers (which is practically always the case when administered directly to the mouth of a patient), these polymers are first caused to swell into a gel by the existing amount of water or saliva present. Therefore, these polymers are preferably characterised by an excellent swelling ability. Most preferably, these polymers forming a gel with water are polyacrylic acids and polyacrylates, especially those having a molecular weight of 400,000 to 4 millions.

Especially preferably, the polymers capable of forming a gel with water are acidic polymers because they are able to react directly with the carbon dioxide-releasing compounds when in contact with water or saliva, releasing carbon dioxide. Preferred are acidic polymers containing the carboxyl or sulfuric acid groups such as CARBOPOL®, the tradename for high molecular weight polymers having acrylic acid chains commercially available through the Lubrizol Corporation (Wickliffe, Ohio), and polycarbophils, but also alginic acid having a viscosity of >500 mPa·s at a pH value of about 7 and a molecular weight of about 200,000, caragheens having a viscosity of at least 1000 mPa·s (2% solution) and pectins, the latter being used if slow swelling is desired.

Preferred non-acidic polymers according to component b) (i) are polyethylene oxide having a molecular weight of 4 millions to 7 millions and a viscosity of a 2% solution of 1,000 to 10,000 mPa·s; xanthan (neutralised to a pH value of >6.0) having a viscosity of 1,000 to 3,000 mPa·s, a pH of about 6 and a molecular weight of more than 100,000; sodium carboxymethyl cellulose having a viscosity of 500 to 8,000 mPa·s, preferably 2,000 to 8,000 mPa·s with a degree of polymerisation of 500 to 2,000 and a degree of substitution of not more than 3, i.e. a maximum of 3 carboxymethyl groups per anhydroglucose unit; cellulose ether having a viscosity of 1,000 to 10,000 mPa·s, a degree of polymerisation up to 2,000 and a degree of substitution of not more than 3, such as hydroxyethyl cellulose, hydroxypropyl cellulose, methylhydroxypropyl cellulose having a degree of substitution of 1 to 2, preferably a methylhydroxyl content of 18 to 32% and a hydroxypropyl content of 7 to 15%.

Most preferred for the component b) (i) are carbomers (designation according to the European Pharmacopoeia) which are distributed under the designation CARBOPOL® (as far as the inventors are aware, they are homopolymers of acrylic acids which are usually cross-linked with allyl pentaerethrythol) and polycarbophil; i.e. homopolymers of acrylic acid crosslinked with divinyl glycol. As a 1% aqueous solution or dispersion, these compounds have a pH value of 2.0 to 3.0 and can thus easily react with alkali/alkaline earth hydrogen carbonates/carbonates. In the invention, polymers which not only form a gel with water, but which also are soluble in gastric juice, i.e. at a pH value of less then 3.5, or in which the colloidal disperse gel undergoes a severe degradation of viscosity in gastric juice are especially preferred as component b) (i), because a particularly rapid release of the cores containing the active ingredient (optionally with additional coatings) in the stomach can be guaranteed.

Other polymers capable of forming a gel with water and preferred in the invention are those which are acidic and which swell considerably as the pH value increases, decreasing their viscosity as the pH value decreases. In particular, these are polyacrylic acids (like the commercial product CARBOPOL®), cross-linked polyacrylic acids such as polycarbophil and alginic acids. However, typical cellulose ethers such as methyl cellulose, hydroxyethyl cellulose, hydroxypropyl cellulose and hydroxypropyl methyl cellulose and ionic polymers such as sodium carboxy methyl cellulose, pectin, xanthan, galactomanan, guar gum, hydroxypropyl guar gum, sodium alginate and such like are also suitable, if they are capable to form a gel with water.

The polymers capable of forming a gel with water preferably have a mean grain size of 0.25 mm maximum, typically 0.05 to 0.1 mm. If the fastest possible and uniform formation of a soft, but mechanically stable particle surface is desired, a very small grain size is preferably selected. As a rule, gel-forming polymers having a mean grain size of 50 μm maximum, most preferably 1 to 25 μm are used.

The compound according to b) (ii), i.e. the polymer which is not capable of forming a gel in water is most preferably a EUDRAGIT® polymer, especially a Type E EUDRAGIT® polymer, the tradename for a polymethacrylate-based copolymer commercially available through Evonik Industries AG (Essen, Germany). For a definition of the EUDRAGIT® polymers, reference is made to "Fiedler, Lexikon der Hilfsstoffe zur Pharmazie, Kosmetik and angrenzende Gebiete, 5$^{th}$ ed., 2002". Especially preferably, the polymers not capable of forming a gel with water are a copolymer of cationic nature on the basis of dimethylaminoethyl methacrylate and neutral methacrylic acid esters which often have a mean weight average molecular weight of approx. 150,000. The compounds are also known under the chemical designation poly(butylmethacrylate, (2-dimethylaminoethyl)methacrylate, methyl methacrylate) 1:2:1. Even though the polymer EUDRAGIT® E is especially preferred, other polymers may be used as component b) (ii), such as EUDRAGIT® E30D, EUDRAGIT® RS and EUDRAGIT® RS30D, EUDRAGIT® RL, and EUDRAGIT® RL30D, as well as ethyl cellulose and cellulose acetate. While EUDRAGIT® E is soluble at a pH value of less than 5 and therefore also in gastric juice, some of the other polymers listed above are not soluble in gastric juice. In that case, the ratio between the polymer capable of forming a gel with water, the polymer not capable of forming a gel with water and the carbon dioxide-releasing agents used may be adjusted to ensure that the release in the stomach is hardly decreased. The appropriate ratios may easily be found by routine experimentation. A larger amount of the gel-forming polymer (component b) (i)) vis-à-vis the non-gel-forming polymer used (component b) (ii)) increases release in the gastric juice. A larger amount of the carbon dioxide-releasing compound (especially of the inorganic carbonates) causes the destruction of the coating according to the invention so that it loses its releaseretarding function. Among other things, this is caused by the carbon dioxide development within the coating of the invention if the pellets come into contact with the acidic gastric juice.

The coating according to the invention may also contain acidic components, especially if the polymers used in the coating are not sufficiently acidic to ensure sufficient carbon dioxide development when an inorganic carbonate is used. It goes without saying that these acids may be used additionally if acidic polymers are employed to enhance the $CO_2$ formation. Particularly suitable acids which may be admixed to the coating according to the invention in individual cases are, for example, monosodium hydrogen citrate, adipic acid, fumaric acid any other non-toxic acid common in the pharmaceutical field such as citric acid, tartaric acid, but also monosodium tartrate or, for example, monosodium phosphate.

The components of the coating according to the invention are most preferably selected in such a manner that a 3% dispersion of the coating, i.e. a 3% dispersion of the polymer capable of forming a gel with water, the polymer not capable of forming a gel with water, the carbon-dioxide releasing compound and, optionally, of the acid and additional adjuvants has a pH of at least 4, more preferably a pH of 5.5. This ensures that the non-gel-forming polymer does not dissolve in the mouth. At a low pH value, there is also the risk that the polymers capable of forming a gel with water that may act as thickening agents often exhibit an excessive drop in viscosity which markedly reduces gelling of the polymers.

In accordance with the invention, one or more additional coatings may be present between the core of the pharmaceutical composition containing the active ingredient and the coating according to the invention. In particular, such an additional coating placed between the core and the coating according to the invention may be an enteric or release-controlling coating. Such coatings are well known in the prior art; reference is made to relevant standard books of pharmaceutical technology.

The amounts of the individual components of the coating according to the invention are not particularly limited and may be determined by a skilled practitioner by routine experimentation depending on the specific polymers b) (i) and b) (ii) used and the specific carbon dioxide-releasing compound, the examples of the invention serving as an orientation. However, the ratio between polymer b) (ii) and polymer b) (i) is preferably 10:1 to 1:5, more preferably 3:1 to 1:3 and most preferably 1.5:1 to 1:1.5. The ratio between the soluble polymer and the carbon dioxide-releasing compound is preferably 10:1 to 1:5, more preferably 2:1 to 1:2.

The weight of the coating according to the invention on the cores which contain the active ingredient and which may optionally be coated is 1 to 40%, preferably 3 to 25%, most preferably 6 to 20% based on the total weight of the particles according to the invention.

The coating according to the invention is destroyed by gastric juice (if all polymers used are soluble in gastric juice) or swells to such an extent (if, for example, the polymer according to b) (ii) is insoluble in gastric juice) that it has no influence on the release of the active ingredient. This happens very quickly, preferably in less than 30 minutes, more preferably in less than 10 minutes, especially in less than 5 minutes.

In a preferred embodiment, the pharmaceutical composition of the invention is intended for direct administration into the mouth of a patient, i.e. without being placed in water first. In that case, it is advantageous to administer the pharmaceutical composition according to the invention together with one or more compounds promoting salivation. Therefore, the invention also relates to a medicament which, in addition to the pharmaceutical composition according to the invention, comprises at least one compound promoting salivation. This compound is not a part of the pharmaceutical composition (even though the invention does not rule out that the coating according to the invention of the composition according to the invention contains additional components that promote salivation).

The medicament containing the pharmaceutical composition according to the invention may be designed in such a manner that it contains a mixture of the pharmaceutical composition according to the invention and the salivation-promoting compound. This is preferred for the invention. Alternatively, the pharmaceutical composition according to the invention and the saliva-promoting compound may be present separately in the medicament for simultaneous administration, or the pharmaceutical composition according to the invention may be accompanied by the instruction to take it together with a compound promoting salivation.

In general, any pharmaceutically acceptable substances inducing strong salivation may be suitable for the component generating instant salivation. Water-soluble adjuvants which have a pleasant and sweet taste and are effective owing to their osmotic effect are especially well suited for this purpose. In addition to sucrose, glucose and maltodextrin, non-cariogenic adjuvants such as sorbitol, mannitol, xylitol, maltitol, malbitol, inulin and isomalt are especially suitable. The solubility in water at 37° C. is at least 5%, preferably more than 15%. However, sweeteners such as aspartame, acesulfam K, sodium cyclamate, saccharine and its salts also generate an astonishing degree of spontaneous salivation. Spontaneous salivation is stimulated reflexively by added flavours such as lemon flavour or grapefruit flavour. The flavours sold under the name Optaflow (Symrise) which, for example, induce increased salivation after two minutes which is more pronounced than the salivation caused by sour citric acid are of particular interest. Long-lasting and retarded salivation is particularly advantageous, because additional saliva is formed after the main bulk of the particles containing the active ingredient has been swallowed to facilitate swallowing of the remaining particles.

Spontaneous and strong salivation is also induced by water-soluble organic acids such as tartaric acid, citric acid, malic acid, ascorbic acid and such like and water-soluble salts thereof, especially sodium and potassium salts such as sodium or potassium hydrogen tartrate, sodium hydrogen citrate or sodium ascorbate.

In numerous tests, it was found that the amount of saliva necessary for swallowing depends on the amount of saliva already present in the mouth and the particle size of the particles having the soft, but stable surface according to the invention. Particles of a size up to approx. 2.5 mm in diameter may be swallowed easily. It is interesting to note that particles smaller than about 0.5 mm are adsorbed more easily to the tongue and mucous membrane of the mouth because of their size so that more saliva is necessary to remove all of the particles containing the active ingredient from the oral cavity. In case of particles having a diameter of approx. 2.5 mm and more it may also happen that some particles remain after the first swallowing act so that, again, more saliva is needed to fully remove them from the oral cavity. The amount of saliva from the salivation-promoting adjuvant results from the composition and amount thereof. For example, it is certainly appropriate to add 1.5 to 2.5 g of a tasty salivationgenerating adjuvant mixture to 50 mg of the particles containing the active ingredient. Likewise, it is possible to quantitatively swallow approx. 1 g of particles containing the active ingredient and having a soft, smoothed surface with the aid of saliva generated by approx. 50 mg of citric acid. The ratio of the weight of the pharmaceutical composition according to the invention to the weight of the salivation-inducing compound therefore is preferably 1:50 to 10:1, preferably 1:5 to 1:1. It goes without saying that several salivation-inducing compounds may be used in admixture.

If the coating according to the invention contains only or mostly polymers soluble at a low pH value, as is the case when EUDRAGIT® E which is especially preferred for the invention is used as component b) (ii), difficulties may occur when the salivation-inducing compound makes the pH value in the mouth very low. In that case, it may be advantageous to add an alkaline component such as trisodium citrate or trisodium phosphate. This prevents premature dissolution of the coating according to the invention. The pH value of the saliva itself is neutralised within seconds after ingestion and the desired strong salivation caused by the acid and is raised into a range where the EUDRAGIT® E is insoluble.

Preferred embodiments of the invention are described below. These preferred embodiments are not intended to be limiting.

In a preferred embodiment, a suspension of the dissolved saliva-resistant EUDRAGIT® E is mixed with the preferred polymer polyacrylic acid (CARBOPOL® 971P) and preferably alkaline compounds such as sodium hydrogen carbonate, potassium hydrogen carbonate, calcium carbonate and magnesium carbonate which quickly form carbon dioxide in the presence of an acid and sprayed onto the uneven, often rough-edged crystals or particles with a rough surface. Even if individual particles remain in the mouth, they still have a stable and soft surface which is perceived as pleasant after 30 minutes. This behaviour differs fundamentally from embodiments of the prior art where the swollen polymer is often rubbed off the particles/cores by a brief movement of the tongue or where the concentration of the swelling polymer on the particle surface is so strong that coated particles agglutinate into a highly viscous pellet paste or stick to the palate and teeth when coming into contact with saliva.

The gel-forming polymer incorporated into the non-gel-forming polymer is preferably acidic and reacts with the bicarbonates/carbonates when it comes in contact with saliva, forming carbon dioxide and raising the pH. As a result of the formation of a salt of this polymer, its viscosity increases sharply, and the escaping carbon dioxide bubbles (approx. 50 μm diameter) assist rapid smoothing of the particle surface. Such smoothing or rounding of the particles with their rough-edged surface perceived as sandy or grainy in the mouth is due to the extension of the polymer framework caused by the swelling of the polyacrylic acid and escaping $CO_2$ micro-bubbles. The swollen polymer does not escape from the polymer framework and no gel-like or sticky particle surface is formed. As soon as a sticky and/or gel-like surface is formed, the mechanical stability of a soft particle surface is insufficient, i.e. a few movements of the tongue suffice to remove it. However, this mechanical stress between the particle surface and the tongue and between the palate, particle and tongue is inevitable to transport practically all of the particles into the stomach. Especially with young children, uncontrollable stress on the particle surface must be assumed. In the pharmaceutical composition according to the invention, particles remaining in the oral cavity still have a soft particle surface after 10 to 20 minutes and do not result in a grainy or sandy feeling which might result in the refusal to take it.

These characteristics of the particle surface are novel vis-à-vis the prior art, because agglutination of the particles is avoided and there is practically no adhesion of the particles to the palate or teeth. In particular, it should be emphasised that the soft particle surface perceived as pleasant in the oral cavity is mechanically stable and will not be rubbed off even by tongue movements. In the pH range of saliva of approx. 5.0 to 7.0, the viscosity of the gel-forming polymer according to b) (i) is preferably at its highest. As the pH decreases, however, especially to or below 3.5, the polymer of the most preferred embodiment where the non-gel-forming polymer b) (ii) is soluble in gastric juice dissolves at an increasing rate and the viscosity of the gel-forming polymer b) (i) also decreases. In the acidic environment of the stomach, the excess of $CO_2$-forming adjuvants assists in the dissolution process of the coating of the invention so that the release of the active ingredient is practically not inhibited. This is a special advantage of the coating of the invention because, despite the stability and pleasant mouth-feel of the particles and excellent resistance to saliva, it can easily release the active ingredient when the pH value decreases (unless it is desired to control the release of the active ingredient from the core through a layer positioned under the coating according to the invention).

The speed of the formation of a soft, but stable particle surface is controlled in the invention by the swelling behaviour, the swelling rate of the polymers used, the amount of carbonate/hydrogen carbonate added, the ratio between the non-gel-forming polymer and the gel-forming polymer and the amount of acid available for $CO_2$ formation. If the gel-forming polymer used is not sufficiently acidic or if it is desired to accelerate the formation of carbon dioxide, the formation of a soft particle surface may be assisted by adding a small amount of acid which causes additional carbon dioxide formation together with the excess of hydrogen carbonate/carbonate present. In a manner of speaking, the tiny gas bubbles blow up the layer of non-gel-forming polymer and gel-forming polymer and assist in the formation of a soft, but mechanically stable particle surface perceived as pleasant in the mouth. Since saliva itself usually is neutral to slightly acidic and since hydrogen carbonates/carbonates are also present, there is no risk of this polymer dissolving in the mouth when EUDRAGIT® E, which is soluble in acid is used. The small amounts of acid preferably react with the excess of hydrogen carbonates/carbonates and are neutralised within fractions of a second, forming $CO_2$.

When a polymer soluble in gastric juice such as EUDRAGIT® E is used as component b) (ii), the ratio between polymer b) (ii), polymer b) (i), the $CO_2$-releasing compound and, optionally, an acidic compound is preferably adjusted in such a manner that a 3% aqueous dispersion from said components has a pH value of 5.5 in order to avoid premature dissolution in the mouth. In case of saliva-resistant polymers not soluble in an acidic environment as component b) (ii), on the other hand, the pH value of a 3% aqueous dispersion of said components is adjusted in such a manner that a pH of preferably at least 4 is achieved. The reason for this adjustment is essentially that these soluble polymers display a marked drop in viscosity below a pH value of 4 in an aqueous solution.

Generally, the above-mentioned non-gel-forming polymers b) (ii) are dissolved in an organic solvent such as ethanol, isopropanol, acetone or mixtures thereof. The gel-forming polymers b) (i), the $CO_2$-releasing compound, optionally the above-mentioned, preferably micronised compounds and other typical adjuvants which are used for the preparation of coatings, such as plasticizers and anti-stick agents such as talcum, colouring agents such as iron oxide pigments and titanium dioxide are suspended in solutions of the non-gel-forming polymer b) (ii). The suspensions are sprayed in a known manner, preferably in a fluid bed, onto the fluidised cores of active ingredient. The coating process takes place easily under the well-known conditions for feed air quantity, feed air temperature, and spray rate.

However, it is also possible to initiate strong movement of the active ingredient cores to be coated in a suitable device, for instance a spheroniser, and to spray them with a solution of the insoluble polymer b) (ii). As soon as all particles have been humidified uniformly with the solution, the micronised powder mixture of the soluble polymer b) (i), the $CO_2$-releasing compounds, anti-stick agents, colouring pigments and, optionally, micronised acid is glued onto the particles and sprayed with additional solution. This process is repeated until the entire powder mass has been applied. In this manner, it is also possible to incorporate the gel-forming polymer b) (i) and the adjuvants into the framework of the non-gel-forming polymer b) (ii) with sufficient homogeneity so that, after drying and contact with saliva, a soft, mechanically stable particle surface is also created very quickly in the mouth.

According to the invention, a skilled practitioner is able to control the extent of the particle volume increase in the mouth, the perceived softness of the particle surface and the mechanical stability of the soft particle surfaces in many different ways. If, for example, very fast formation of a soft surface is desired, he will increase the ratio between the non-gel-forming polymer b) (ii) and the gel-forming polymer b) (i) in favour of the gel-forming polymer and use a polymer which forms a gel quickly and intensively for this purpose. Alternatively or in addition, the skilled practitioner may also increase the amount of $CO_2$-forming compounds and the amount of acid in the coating. If it is intended, on the other hand, that particles of a particularly bitter active ingredient some of which may be left in the mouth after an hour still have a soft surface which is perceived as pleasant and makes swallowing easy, he will increase the amount of non-gel-forming polymer b) (ii) vis-à-vis the gel-forming polymer b) (i), refrain from using an acidic polymer or reduce the amount of acid for forming $CO_2$. However, he can also use a gel-forming polymer b) (i) for which a slow gel-forming rate is characteristic. However, in order to obtain a particle surface which both forms quickly and remains soft for a long period of time after ingestion of the particles, the skilled practitioner could use a combination of slow- and fast-gel-forming polymers as the gel-forming polymer b) (i). In this case, for example, the combination of CARBOPOL® 971P which forms a gel quickly and intensely with a cellulose ether that forms a gel slowly, but is highly viscous, namely methyl hydroxy propyl cellulose KM 100 (Methocel KM 100) is suitable for the polymer b) (i). In any case, it is undesirable that a sticky to gel-like, severely swollen, weakly adhering surface is created on the particles, because this might be rubbed off by movement of the tongue after a short residence time in the oral cavity and separate completely from the particles so that the grainy, sandy particle surface which is perceived as unpleasant re-emerges.

According to the invention, it is also possible, for example, to incorporate micronised potassium hydrogen carbonate and micronised calcium carbonate into the coating according to the invention. Upon ingestion, the potassium hydrogen carbonate with its high solubility in water will react immediately with the acidic polymer and contribute to the desired smoothing, whereas calcium carbonate will preferably react with the far more acidic gastric acid after the particles have been swallowed and will thus contribute to a rapid release of the active ingredient by fast destruction of the soft coating according to the invention as a result of $CO_2$ formation.

According to the invention, it is possible for the skilled practitioner to influence the thickness, the speed of the expansion, the softness and the mechanical stability of the coating according to the invention which is perceived as pleasant in the mouth. The composition of the selected coating also makes a significant contribution to its destruction under the influence of gastric juice and thus to a faster release of the active ingredient.

In the invention, it is possible to provide mixtures of fast-releasing and, for example, retarded active ingredient particles with the coating according to the invention. As a rule, however, these are particles containing the active ingredient which is to be released in the stomach as quickly as possible after direct application in the mouth. Therefore, it is important that, despite an optimal feeling in the mouth, the coating according to the invention does not obstruct, but rather promotes the release of the active ingredient in the stomach. This is not assured in the known saliva-resistant coatings which contain small amounts of a water-soluble polymer. In these known embodiments, the water-soluble polymer has the sole function of influencing the release of the active ingredient. As a rule, the prior art uses practically non-gel-forming, but exclusively water-soluble polymers such as hydroxy propyl methyl cellulose which, as a 2% solution, have a viscosity of not more than 50, preferably 3 to 6 mPa·s. In no instance is the fast smoothing of the particle surface by the formation of a soft, mechanically stable coating which is perceived as pleasant in the mouth achieved or intended.

Ethyl cellulose is often used as a saliva-resistant polymer in the prior art. This is insoluble in the stomach so that the fast release of the active ingredient is delayed even if a water-soluble polymer is incorporated into the ethyl cellulose unless a large amount of water-soluble polymer is used. According to the invention, the $CO_2$-forming compound which reacts not only in the mouth, but also in the stomach, ensures that the coating according to the invention is either destroyed in the stomach or swells to such an extent that the release of the active ingredient is not affected. If, for instance, there is another layer, e.g. a retard layer controlling the release of the active ingredient under the coating according to the invention, the desired release of the active ingredient according to the retard layer is practically not affected as a result of the fast separation of the coating of the invention. For example, this also applies for particles which have an enteric layer under the coating according to the invention.

The ratio between the components non-gel-forming polymer b) (ii), gel-forming polymer b) (i), $CO_2$-forming compound and an optional acid is suitably selected in such a manner that the gel-forming polymer b) (i) expands the polymer framework of the non-gel-forming polymer b) (ii) with the support of the $CO_2$ micro-bubbles in the mouth of the patient, but remains enclosed in the polymer framework. The gel-forming polymer does not escape from the saliva-resistant swollen coating and does not cause a sticky effect on the surface which glues the particles together in the mouth. However, it was surprising for the skilled practitioner that a volume increase of the particles by 30% still takes place within 30 seconds and a soft smoothed surface is generated, which is easy to swallow and perceived as pleasant in the mouth and which is able to withstand the mechanical stress in the mouth for more than 30 minutes. In water (pH 7.0, 37° C.), the volume increase after 4 minutes is at least 50%, more preferably about 100%

For example, the pharmaceutical composition according to the invention may be introduced directly into the mouth with a little water. Preferably, however, the pharmaceutical composition according to the invention is mixed with the saliva-forming component and bagged into so-called "stick packs" and then introduced directly into the mouth, preferably onto the middle of the tongue, from the stick packs without water. In order to achieve a high dosage accuracy, it is also possible to bag one or more particles containing one or more active ingredients separately from the saliva-forming mixture into the stick packs. Special dosing devices are capable of bagging particles containing the active ingredient separately from the saliva-forming mixture into the same stick pack simultaneously. However, the coated particles containing the active ingredient and the saliva-forming mixture may also be mixed or introduced separately into special hard gelatine capsules or bagged, for example, in sachets that are easy to open. The contents are then poured directly onto the tongue by the patient. In general, however, so-called stick packs are especially preferred as primary packages, because the stick packs made of aluminium-backed foils are completely tight and protect the contents perfectly against humidity. In addition, the contents may be placed into the mouth easily after the elongated, only 1 to 2 cm wide stick packs are opened. However, the drug may also consist of a mixture of particles containing the active ingredient prepared according to the invention and the saliva-forming component which, for example, is canned or bottled. The mixture is then poured into the mouth with the aid of a dosing spoon. In accordance with the invention, it is also possible to pack the pharmaceutical composition according to the invention and the saliva-forming compound separately with the instruction to administer them together.

Finally, the particles of the invention may also be poured into a glass of water where they disperse easily and float as a result of an increase in volume so that the floating particles may easily be drunk with water.

The invention is further illustrated by the following examples, which are merely intended to illustrate the principles of the invention. Those skilled in the art will recognize that variations and modifications may be made to the embodiments without changing the principles of the invention herein disclosed. Accordingly, the examples described in detail below are in no way intended to limit the scope of the present invention.

EXAMPLES

Example 1

1a) Preparation of Guaifenesine Pellets

| Guaifenesine | (1) | 100.0 kg |
|---|---|---|
| Microcrystalline cellulose | (2) | 102.0 kg |
| Povidone K25 | (3) | 8.0 kg |

The three components (1) to (3) are mixed in a suitable wet-mixing device and humidified with 30 kg of water. The resulting workable mass is extruded and rounded into pellets with a grain size range from 0.4 go 1.6 mm in a spheroniser.

1b) Preparation of Saliva-Resistant Guaifenesine Pellets

After drying, the particles are provided with the following coating layer:

| EUDRAGIT ® E | (1) | 12.1 kg |
|---|---|---|
| Triethyl citrate | (2) | 1.0 kg |
| Talcum | (3) | 22.1 kg |
| Magnesium stearate | (4) | 1.4 kg |
| Ethanol | (5) | 101.0 kg |
| Water | (6) | 8.0 kg |

(1) and (2) are dissolved and (3) and (4) suspended in a mixture of (5) and (6). The suspension is sprayed in a well-known manner onto the particles containing 210 kg of guaifenesine from example 1a) (=246.6 kg of guaifenesine pellets, saliva-resistant).

1c) Preparation of Guaifenesine Pellets with a Coating According to the Invention

| EUDRAGIT ® E | (1) | 9.0 kg |
|---|---|---|
| CARBOPOL ® 971P | (2) | 7.2 kg |
| Talcum | (3) | 3.7 kg |
| Stearic acid | (4) | 1.8 kg |
| Sodium hydrogen carbonate | (5) | 7.2 kg |
| Ethanol | (6) | 116.0 kg |

(1) and (4) are dissolved and (2), (3) and (5) suspended in ethanol (6). The suspension is sprayed onto the 246.6 kg of saliva-resistant guaifenesine pellets of example 1b) in a well-known manner in a fluid bed. After drying, 275.5 kg of guaifenesine pellets according to the invention are obtained (10.5% of coating according to the invention).

1d) The particles of the invention prepared in 1c) have a soft layer which is perceived as pleasant in the mouth, but is still mechanically stable. This stability is still preserved after 30 minutes and withstands mechanical stress by rubbing with the tongue. The smoothing of the particle surface which takes place surprisingly fast in the eyes of the skilled practitioner is demonstrated in the following experiment.

A certain amount of the particles prepared in example 1c) is poured into a 250 ml measuring cylinder filled with water of approx. 37° C., and the volume of the settled particles determined within 5 seconds. After certain intervals, the volume increase resulting from the expansion and smoothing of the particle surface is determined.

| Particle volume in water, 37° C. | | | | | | |
|---|---|---|---|---|---|---|
| Beginning | 0.5 min | 1 min | 2 min | 3 min | 4 min | 5 min |
| 70 ml | 93 ml | 100 ml | 116 ml | 128 ml | 136 ml | 142 ml |
| 72 ml | 98 ml | 104 ml | 118 ml | 132 ml | 140 ml | 144 ml |
| 68 ml | 96 ml | 106 ml | 120 ml | 134 ml | 142 ml | 142 ml |
| 75 ml | 88 ml | 108 ml | 116 ml | 138 ml | 146 ml | 156 ml |
| 70 ml | 92 ml | 104 ml | 112 ml | 140 ml | 145 ml | 148 ml |
| Mean values | | | | | | |
| 71 ml | 93 ml | 104 ml | 116 ml | 134 ml | 142 ml | 147 ml |

If the experiment is repeated with the particles from example 1b) not coated according to the invention, the particle volume will increase from an initial 70 ml to only 72 ml after 4 minutes.

It is unexpected for the skilled practitioner that after an average of only 30 seconds a volume increase of more than 30% occurs as a result of expansion and smoothing of the particles surfaces and that the volume of the particles has increased by 100% after only 3 to 4 minutes. Looking at the volume increase of the particles under a microscope, smooth, even particle surfaces are shown from which individual gas bubbles of approx. 50 μm escape. The particles are not perceived as foreign bodies in the mouth itself, because the surfaces are smooth, soft and ductile, but still so stable mechanically that the smoothed surface cannot be removed by movement of the tongue or by pressing against the palate. Even particles that may have slipped between the teeth by accident and re-emerge into the oral cavity after 30 minutes still have that pleasant feeling in the mouth.

The particles of the invention thus expand in water of 37° C. within 30 seconds to a volume increased by 30% and form a soft, smooth pellet surface. The pellets are individually dispersed and do not stick together. They have the tendency to float. If the particles are removed from the water after 5 minutes, the coating according to the invention cannot be destroyed by slight pressure with a spatula. The smooth, soft outer layer may be removed from the hard inner active ingredient core only by significant mechanical stress such as rubbing between thumb and index finger.

If the particles are taken into the mouth, the tongue will feel a smooth, soft and even surface without any sandy or grainy feeling after 30 seconds at the latest. Said latter feeling comes immediately when the saliva-resistant guaifenesine pellets 1b) without the coating according to the invention are placed into the mouth. Even after 30 minutes, the particles 1c) according to the invention still have a stable, soft and unbroken surface which is perceived as very pleasant, but is still stable when touched with the tongue.

1e) A dissolution test was carried out in artificial gastric juice according to the U.S. Pharmacopoeia, paddle method, 50 rpm. The result is shown in FIG. 1 which shows the release values of guaifenesine pellets 1a), pellets 1b) not coated according to the invention and pellets 1c) according to the invention.

Despite the additional coating, the release of the active ingredient from the guaifenesine particles 1c) according to the invention is surprisingly not reduced vis-à-vis the saliva-resistant particles 1b). As a result of the volume increase of the particles 1c), these begin to float, so that they are moved around more intensely in the dissolution medium and thus surprisingly display a faster release of the active ingredient vis-à-vis 1b).

As desired, the guaifenesine release in water is very low. Even after a residence time in water of 5 minutes, only 1% of the active ingredient is released.

Example 2

The following components of the invention promoting salivation:

| | | |
|---|---|---|
| Sorbitol, 0.1-1.0 mm | (1) | 558.0 kg |
| Sodium carboxymethyl cellulose | (2) | 10.0 kg |
| Aspartame | (3) | 2.0 kg |
| Tutti-Frutti flavour (650916, Symrise) | (4) | 7.0 kg |
| Banana flavour (214746, Symrise) | (5) | 2.0 kg |
| Magnesium stearate | (6) | 3.0 kg | are screened through a sieve with a mesh width of 1.5 mm and mixed for 15 minutes.

The amount of saliva formed upon ingestion of 582 mg of the salivation-promoting mass according to example 2 was tested on 10 test persons. 30 seconds from the ingestion 2.3 ml of saliva had formed (range from 1.8 to 3.2 ml). It is completely sufficient for swallowing the amount of 278 mg guaifenesine particles 1c) according to the invention.

Example 3

Stick Pack Bagging 275.5 kg of the guaifenesine pellets 1c) are mixed with 1 kg of magnesium stearate and 1.5 kg of talcum. By means of a two-chamber dosing slider on a bagging machine, 278 mg of this mixture are bagged into a stick pack with 582 mg of the salivation-promoting component according to example 2 and sealed. The net weight is 860 mg and contains 100 mg of guaifenesine. The ratio of the guaifenesine pellets according to the invention to the salivation-promoting mixture is 1:2.1.

Example 4

Following example 1a) and 1b) exactly, 171 kg of saliva-resistant guaifenesine pellets containing 50 kg of guaifenesine are prepared.

Example 5

Preparation of Guaifenesine Pellets with a Coating According to the Invention

| | | |
|---|---|---|
| Guaifenesine pellets (acc. to example 4) | (1) | 171 kg |
| EUDRAGIT ® E | (2) | 5.9 kg |
| CARBOPOL ® 971P | (3) | 4.7 kg |
| Talcum | (4) | 2.5 kg |
| Stearic acid | (5) | 1.2 kg |
| Sodium bicarbonate | (6) | 4.7 kg |
| Ethanol | (7) | 75.0 kg |

Following example 1c) exactly, the dispersion is prepared from the components and sprayed onto the saliva-resistant guaifenesine pellets of example 4=190 kg of pellets according to the invention (10.6% of the coating according to the invention). They are mixed with 1 kg of magnesium stearate and 1 kg of talcum.

Example 6

Salivation-Promoting Mixture According to the Invention

| | | |
|---|---|---|
| Sorbitol, 0.1 bis 1.0 mm | (1) | 276.0 kg |
| Sodium carboxy methyl cellulose | (2) | 5.0 kg |
| Grape flavour (208275, Symrise) | (3) | 3.0 kg |
| Raspberry flavour (652742, Symrise) | (4) | 1.0 kg |
| Aspartame | (5) | 1.0 kg |
| Magnesium stearate | (6) | 3.0 kg |

According to examples 2 and 3, 192 mg each of the pellets according to the invention of example 5 are bagged into a stick pack together with 289 mg of the salivation-promoting mixture of example 6. The net weight is 481 mg and contains 50 mg of guaifenesine. The ratio of the guaifenesine pellets according to the invention to the salivation-promoting mixture is 1:1.5.

Within 30 seconds after oral ingestion, approx. 1.5 ml of saliva is formed in the mouth which is completely sufficient for swallowing 192 mg of guaifenesine pellets according to the invention.

Example 7

7a) Caffeine Particles with a Saliva-Resistant Layer

Compacted caffeine particles of a mean particle size of 0.3 mm are coated with an EUDRAGIT® coating exactly as in example 1b). The weight of the coating is 10.8%.

7b) Preparation of Caffeine Particles Having a Coating According to the Invention

| Caffeine particles 7a) | (1) | 4000 g |
| --- | --- | --- |
| EUDRAGIT ® E | (2) | 300 g |
| CARBOPOL ® 971 P | (3) | 240 g |
| Talcum | (4) | 125 g |
| Stearic acid | (5) | 60 g |
| Sodium hydrogen carbonate | (6) | 240 g |
| Ethanol | (7) | 3800 g |

A suspension is prepared in accordance with example 1c) and sprayed on in a well-known manner in a fluid bed. After drying, 4,965 g of caffeine particles according to the invention (19.4% of the coating of the invention) are obtained.

The volume of the particles in water of 37° C. expands by 35% within 30 seconds. After only three minutes, the final expansion of 85% is achieved. If these particles are taken into the mouth, a pleasant, soft, but mechanically stable, smooth surface can be felt within 15 seconds by touching them with the tongue or pressing them against the palate. These particles are not perceived as foreign bodies in the mouth and can be swallowed with great ease. Individual particles left in the mouth do not taste bitter and show a soft, unbroken surface when touched with the tongue or the palate.

In the dissolution test described in example 1e), a caffeine release of more than 90% is obtained after 15 minutes in artificial gastric juice. The particles show a marked tendency to float owing to the volume increase of the particles.

7c) Salivation-Promoting Component According to the Invention

| Sorbitol 0.1 bis 1.0 mm | (1) | 14.0 kg |
| --- | --- | --- |
| Sodium carboxy methyl cellulose | (2) | 0.3 kg |
| Sucralose | (3) | 0.06 kg |
| Cappuccino flavour (142618, Symrise) | (4) | 0.1 kg |
| Magnesium stearate | (5) | 0.15 kg |
| Talcum | (6) | 0.15 kg | are screened through a sieve with a mesh width of 1.5 mm and mixed for 15 minutes.

7d) Stick Pack Bagging 4,965 g of the caffeine particles 7b) according to the invention are mixed with 50 g of magnesium stearate and 50 g of talcum. By means of a two-chamber dosing slider in a bagging machine, 284 mg of this mixture are bagged into a stick pack together with 828 mg of the salivation-promoting component 7d) in a single operation and sealed. The total net weight is 1,112 mg and contains 200 mg of caffeine. The ratio of the caffeine particles according to the invention to the salivation-promoting mixture is 1:2.9.

Example 8

8a) Preparation of Guaifenesine/Dextromethorphan Pellets

| Guaifenesine | (1) | 100.0 kg |
| --- | --- | --- |
| Dextromethorphan | (2) | 5.0 kg |
| Microcrystalline cellulose | (3) | 100.0 kg |
| Polyethylene glycol 6000 | (4) | 10.0 kg |
| Povidone K 25 | (5) | 8.0 kg |

The four components (1 to 4) are mixed in a suitable wet-mixing device and humidified with 23 kg of water. The resulting mass is extruded and rounded in a spheroniser to pellets of a grain size range of 0.6 to 1.6 mm.

8b) Preparation of Saliva-Resistant Guaifenesine/Dextromethorphan Pellets

After drying, 223 kg of 8a) are provided with the following coating:

| EUDRAGIT ® E | (1) | 10.4 kg |
| --- | --- | --- |
| Triethyl citrate | (2) | 0.5 kg |
| Talcum | (3) | 6.0 kg |
| Magnesium stearate | (4) | 1.2 kg |
| Ethanol | (5) | 75.0 kg |
| Water | (6) | 5.0 kg |

According to example 1b), the suspension is sprayed in a well-known manner onto 223 kg of guaifenesine/dextromethorphan particles=241.1 kg of guaifenesine/dextromethorphan pellets, saliva-resistant.

8c) Preparation of Guaifenesine/Dextromethorphan Pellets with a Coating According to the Invention

| EUDRAGIt ® E | (1) | 10.0 kg |
| --- | --- | --- |
| CARBOPOL ® 971P | (2) | 11.0 kg |
| Talcum | (3) | 3.0 kg |
| Stearic acid | (4) | 1.5 kg |
| Sodium hydrogen carbonate | (5) | 10.0 kg |
| Ethanol | (6) | 106.0 kg |

According to example 1d), the suspension prepared is sprayed in a well-known manner onto 241.1 kg of saliva-resistant guaifenesine/dextromethorphan pellets in a fluid-bed apparatus. After drying, 276.6 kg of pellets according to the invention (12.8% coating according to the invention) are obtained. The pellets according to the invention expand in water of 37° C. within 30 seconds with a volume increase of 39% and form a soft, smooth pellet surface. The pellets are dispersed individually and do not agglutinate. After only 5 seconds, a soft, smooth, mechanically stable surface is felt in the mouth which cannot be destroyed by touching with the tongue or pressing against the palate. The particles are not perceived as foreign bodies in the mouth and may be swallowed easily.

8d) Salivation-Promoting Component According to the Invention

| Sorbitol, 0.1 bis 1.0 mm | (1) | 558.0 kg |
| --- | --- | --- |
| Sodium carboxy methyl cellulose | (2) | 10.0 kg |
| Aspartame | (3) | 2.0 kg |
| Tutti-Frutti flavour (650916, Symrise) | (4) | 7.0 kg |
| Banana flavour (214746, Symrise) | (5) | 2.0 kg |
| Magnesium stearate | (6) | 3.0 kg | are screened through a sieve with a mesh width of 1.5 mm and mixed for 15 minutes.

8e) Stick Pack Bagging 276.6 kg of the guaifenesine/dextromethorphan pellets 8c) are mixed with 1 kg of magnesium stearate and 1.4 kg of talcum. By means of a two-chamber dosing slider in a bagging machine, 279 mg of this mixture are bagged into a stick pack together with 582 mg of the salivation-promoting component according to example 3 in a single operation and sealed. The total net weight is 861 mg and contains 100 mg of guaifenesine and 5 mg of dextromethorphan. The ratio of the guaifenesine according to the invention to the salivation-promoting mixture is 1:2.1.

In the same way, 139.5 mg of pellets are bagged together with 291 mg of the salivation-promoting component in one single operation. The total net weight is 430.5 mg and contains 50 mg of guaifenesine and 2.5 mg of dextromethorphan.

8f) In the dissolution test according to the Pharmacopoeia, paddle method, 50 rpm in artificial gastric juice, more than 90% of both guaifenesine and dextromethorphan are released within 20 minutes. The pellets show a marked tendency to float.

Example 9

9a) Preparation of Guaifenesine/Phenylephrine Pellets

| Guaifenesine | (1) | 100.0 kg |
| --- | --- | --- |
| Phenylephrine | (2) | 5.0 kg |
| Microcrystalline cellulose | (3) | 100.0 kg |
| Polyethylene glycol 6000 | (4) | 10.0 kg |
| Povidone K 25 | (5) | 8.0 kg |

The four components (1 to 4) are mixed in a suitable wet-mixing device and humidified with 23 kg of water. The resulting workable mass is extruded and rounded to pellets having a grain size in the range from 0.6 to 1.6 mm in a spheroniser.

9b) Preparation of Saliva-Resistant Guaifenesine/Phenylephrine Pellets

After drying, 223 kg of 9a) are provided with the following coating:

| EUDRAGIT ® E | (1) | 10.4 kg |
| --- | --- | --- |
| Triethyl citrate | (2) | 0.5 kg |

-continued

| Talcum | (3) | 6.0 kg |
| --- | --- | --- |
| Magnesium stearate | (4) | 1.2 kg |
| Ethanol | (5) | 75.0 kg |
| Water | (6) | 5.0 kg |

According to example 1b), the suspension is sprayed in a well-known manner onto 223 kg of guaifenesine/phenylephrine particles=241.1 kg of guaifenesine/phenylephrine pellets, saliva-resistant.

9c) Preparation of Guaifenesine/Phenylephrine Pellets with a Coating According to the Invention

| EUDRAGIT ® E | (1) | 10.0 kg |
| --- | --- | --- |
| CARBOPOL ® 971P | (2) | 11.0 kg |
| Talcum | (3) | 3.0 kg |
| Stearic acid | (4) | 1.5 kg |
| Sodium hydrogen carbonate | (5) | 10.5 kg |
| Ethanol | (6) | 106.0 kg |

According to example 1d), the suspension prepared is sprayed in a well-known manner onto 241.1 kg of saliva-resistant guaifenesine/phenylephrine pellets 9b) in a fluid-bed apparatus. After drying, 276.6 kg of pellets according to the invention are obtained (12.8% of the coating according to the invention). The pellets according to the invention expand by 36% in volume in water of 37° C. within 30 seconds, forming a soft, smooth pellet surface. The pellets are dispersed individually and do not agglutinate. After only 5 seconds, a soft, smooth, mechanically stable surface is felt in the mouth which cannot be destroyed by touching with the tongue or pressing against the palate. The particles are not perceived as foreign bodies in the mouth and may be swallowed easily.

9d) Salivation-Promoting Component According to the Invention

| Sorbitol, 0.1 bis 1.0 mm | (1) | 558.0 kg |
| --- | --- | --- |
| Sodium carboxy methyl cellulose | (2) | 10.0 kg |
| Aspartame | (3) | 2.0 kg |
| Tutti-Frutti flavour (650916, Symrise) | (4) | 7.0 kg |
| Banana flavour (214746, Symrise) | (5) | 2.0 kg |
| Magnesium stearate | (6) | 3-0 kg | are screened through a sieve with a mesh width of 1.5 mm and mixed for 15 minutes.

9e) Stick Pack Bagging 276.6 kg of the guaifenesine/phenylephrine pellets 9c) are mixed with 1 kg of magnesium stearate and 1.4 kg of talcum. In a 2-chamber dosing slider of a bagging machine, 279 mg of this mixture are bagged into a stick pack together with 582 mg of the salivation-promoting component in a single operation as in example 3 and sealed. The net weight is 861 mg and contains 100 mg of guaifenesine and 5 mg of phenylephrine. The ratio of the guaifenesine/phenylephrine pellets according to the invention to the salivation-promoting mixture is 1:2.1.

In the same manner, 139.5 mg of pellets are bagged with 291 mg of the salivation-promoting component in a single operation. The total net weight is 430.5 mg and contains 50 mg of guaifenesine and 2.5 mg of phenylephrine.

9f) In the dissolution test according to the Pharmacopoeia, paddle method, 50 rpm in artificial gastric juice, more than 90% of both guaifenesine and dextromethorphan are released within 20 minutes. The pellets show a marked tendency to float.

Example 10

10a) Prednisolone Phosphate-Sodium Pellets

| Prednisolone phosphate-sodium | (1) | 125 g |
|---|---|---|
| Povidone K25 | (2) | 100 g |
| EUDRAGIT ® E | (3) | 500 g |
| Talcum | (4) | 100 g |
| Polyethylene glycol 6000 | (5) | 100 g |
| Ethanol | (6) | 4500 g |
| Water | (7) | 900 g |

The components (1), (2), (3) and (5) are dissolved and the component (4) suspended in a mixture of (6) and (7). The suspension is sprayed onto 5000 g of non-pareilles having a particle size of 0.5 to 0.8 mm in a fluid bed=5.925 g of prednisolone phosphate-sodium pellets.

10b) Prednisolone Phosphate-Sodium Pellets with a Coating According to the Invention

| EUDRAGIT ® E | (1) | 300 g |
|---|---|---|
| CARBOPOL ® 971 P | (2) | 200 g |
| Talcum | (3) | 140 g |
| Stearic acid | (4) | 50 g |
| Sodium hydrogen carbonate | (5) | 180 g |
| Calciumcarbonat | (6) | 90 g |
| Ethanol | (7) | 3000 g |

(1) and (4) are dissolved and the components (2), (3), (5) and (6) suspended in ethanol. This suspension is sprayed in a well-known manner onto 5,925 g of prednisolone phosphate-sodium pellets a) in a fluid-bed apparatus. After drying, 6,885 g prednisolone pellets according to the invention are obtained (13.9% of the coating according to the invention, active ingredient content 1.8%).

10c) Salivation-Promoting Component

| Mannitol, spray-dried, 0.05 to 0.4 mm | (1) | 28000 g |
|---|---|---|
| Sorbitol, 0.1 to 1.0 mm | (2) | 11000 g |
| Sodium carboxy methyl cellulose | (3) | 700 g |
| Sucralose | (4) | 700 g |
| Grape flavour (208275, Symrise) | (5) | 500 g |
| Raspberry flavour (652742, Symrise) | (6) | 500 g |
| Magnesium stearate | (7) | 600 g |

10d) In accordance with examples 2 and 3, 139 mg (2.5 mg of prednisolone phosphate-sodium) and 278 mg (5 mg of prednisolone phosphate-sodium) each, respectively, of the particles from example 10b) are bagged into a stick pack with 848 mg of the salivation-promoting mixture from example 10c). The net weight is 987 and 1,126 mg, respectively. The ratio of the prednisolone pellets according to the invention to the salivation-promoting mixture is 1:6.1 (2.5 mg of prednisolone-sodium per stick pack) or 1:3.05 (5 mg of prednisolone phosphate-sodium per stick pack), respectively. If the content of one stick pack is poured onto the tongue, saliva of 2.4 ml on average is formed within one minute. The viscosity of the saliva is increased by the addition of sodium carboxy methyl cellulose. The particles according to the invention are suspended in the saliva. The surface of the particles feels soft and smooth when they are touched with the tongue; the surface according to the invention cannot be removed by tongue movements or pressing against the palate. Practically all of the particles according to the invention may easily be swallowed together with the saliva formed.

Example 11

11a) Saliva-Resistant Paracetamol Particles

| Paracetamol crystals 0.05 to 0.4 mm | (1) | 85.0 kg |
|---|---|---|
| EUDRAGIT ® E | (2) | 10.0 kg |
| Talcum | (3) | 2.0 kg |
| Stearic acid | (4) | 2.0 kg |
| Sodium lauryl sulfate | (5) | 1.0 kg |
| Water | (6) | 60.0 kg |

In a fluid-bed apparatus, paracetamol crystals are coated with an aqueous EUDRAGIT® E suspension having the composition according to 11a) in a well-known manner and dried. 100.0 kg of saliva-resistant paracetamol particles are obtained. These are covered with the coating 11b) according to the invention.

11b) Paracetamol Particles with a Coating According to the Invention

| EUDRAGIT ® E | (1) | 5.9 kg |
|---|---|---|
| CARBOPOL ® 971 P | (2) | 5.0 kg |
| Talcum | (3) | 2.5 kg |
| Stearic acid | (4) | 1.0 kg |
| Sodium hydrogen carbonate | (5) | 2.5 kg |
| Ethanol | (6) | 50.0 kg |

After drying, 116.9 kg of paracetamol particles with the coating according to the invention are obtained. The particles are mixed with 1.1 kg of magnesium stearate. The active ingredient content is 72.0%.

11c) Salivation-Promoting Mixture

| Sorbitol, 0.1 to 1.0 mm | (1) | 100.0 kg |
|---|---|---|
| Sodium carboxy methyl cellulose | (2) | 2.5 kg |
| Cappuccino flavour (142618, Symrise) | (3) | 1.5 kg |
| Salivation-promoting flavour (Optaflow, 150226, Symrise) | (4) | 0.9 kg |
| Sucralose | (5) | 0.5 kg |
| Magnesium stearate | (6) | 1.5 kg |

11d) Amounts of paracetamol particles coated according to the invention which correspond to 250, 500 or 1000 mg of paracetamol are mixed with the salivation-promoting component as shown in the following table and bagged into stick packs. In the case of the stick packs with 1,000 mg of paracetamol, the ratio of the salivation-promoting flavour (Optaflow) according to composition 11c) is increased from 0.9 kg to 1.8 kg.

| Paracetamol | Paracetamol particles according to the invention A | Salivation-promoting component B | Ratio A:B |
|---|---|---|---|
| 250 mg | 347 mg | 300 | 1.16:1 |
| 500 mg | 694 mg | 500 | 1.39:1 |
| 1,000 mg | 1,388 mg | 600 | 2.3:1 |

If the contents of a stick pack are poured into the tongue, the salivation-promoting component dissolves within approx. 30 seconds. Within 30 seconds, the originally sandy, rough-edged paracetamol crystals form a pleasant, soft, but mechanically stable surface with the coating according to the invention. The particles may be swallowed easily with the saliva formed.

Example 12

12a) Acetyl Salicylic Acid Particles with a Coating According to the Invention

| | | |
|---|---|---|
| Acetyl salicylic acid particles 0.05 to 0.4 mm | (1) | 100.0 kg |
| EUDRAGIT ® E | (2) | 6.0 kg |
| CARBOPOL ® 971 | (3) | 4.5 kg |
| Stearic acid | (4) | 1.5 kg |
| Sodium hydrogen carbonate | (5) | 2.0 kg |
| Monosodium citrate, mean grain size 25 μm | (6) | 1.0 kg |
| Ethanol | (7) | 85.0 kg |

In a well-known manner, an ethanolic EUDRAGIT® E suspension is prepared from the components which are sprayed onto acetyl salicylic acid particles in a fluid-bed apparatus. 15 kg of the coating according to the invention are applied onto 100 kg of the acetyl salicylic acid particles. The particles according to the invention are dried carefully. The active ingredient content of the particles is 87%.

12b) Acetyl Salicylic Acid/Paracetamol/Caffeine Stick Packs 250/250/62.5 mg

In a well-known manner, a mixture prepared of 287.4 mg of acetyl salicylic acid particles according to example 12a), 347 mg of paracetamol particles according to example 11b), 87 mg of caffeine particles according to example 7b) and 400 mg of the salivation-promoting component of example 11c) are bagged into a stick pack. The analgesics combination is poured directly onto the tongue from the stick pack and may be swallowed easily together with the saliva formed after 30 seconds. All particles have a soft particle surface perceived as pleasant in the mouth and may easily be swallowed without water.

For the treatment of migraine, packs which contain 500 mg of acetyl salicylic acid, 500 mg of paracetamol and 130 mg of caffeine with the coating according to the invention are prepared in the same manner. The salivation-promoting component 11c) amounts to 500 mg. In order to increase salivation, however, it contains twice the amount the salivation-promoting flavour (Optaflow, Symrise).

The principles of this invention have been described in connection with specific examples and preferred embodiments. However, it should be clearly understood that these descriptions are added only by way of example and are not intended to limit, in any way, the scope of the invention, which is defined by the appended claims and their equivalents.

The disclosure of each publication, patent or patent application mentioned in this specification is specifically incorporated herein by reference herein in its entirety.

The invention claimed is:

1. A pharmaceutical composition for oral administration comprising at least one particle containing an active ingredient, said at least one particle comprising:
   a) a core which contains the active ingredient of the particle and, optionally, suitable adjuvants, and
   b) one or more coating layers applied to the core, such that either a single coating layer, when only one coating layer is present, or an outermost coating layer, when more than one coating layer is present, contains:
      (i) at least one polymer capable of forming a gel with water,
      (ii) at least one polymer not capable of forming a gel with water, wherein said polymer is substantially insoluble in water at a pH of 7.0 and soluble at or below a pH of 3.5,
      (iii) at least one compound capable of releasing carbon dioxide, and
      (iv) optionally, additional adjuvants,
   wherein at least one of the polymers set forth in b)(i) and b)(ii) is an acidic polymer or the single coating layer or outermost coating layer includes an acidic compound, further wherein the weight ratio between the polymer set forth in b) (ii) and the polymer set forth in b) (i) ranges from 3:1 to 1:5.

2. The pharmaceutical composition according to claim 1, wherein the polymer capable of forming a gel with water set forth in b)(i) has a viscosity of at least 5000 mPa·s in a 2 wt.-% aqueous dispersion or solution at a pH of 7.0.

3. The pharmaceutical composition according to claim 1, wherein the polymer not capable of forming a gel with water set forth in b)(ii) has a viscosity of not more than 50 mPa·s in a 2 wt.-% aqueous dispersion at a pH of 7.0.

4. The pharmaceutical composition according to claim 1, wherein the polymer not capable of forming a gel with water set forth in b) (ii) is a copolymer of cationic character on the basis of dimethyl amino methyl methacrylate and neutral methacrylic acid esters.

5. The pharmaceutical composition according to claim 1, wherein the polymer capable of forming a gel with water set forth in b) (i) is a crosslinked polyacrylic acid or a crosslinked polyacrylate.

6. The pharmaceutical composition according to claim 1, wherein the polymer capable of forming a gel with water set forth in b) (i) is a carbomer.

7. The pharmaceutical composition according to claim 1, wherein the compound capable of releasing carbon dioxide set forth in b) (iii) is either (a) a compound of the formula $MH_n(CO_3)$ wherein M is an alkali or alkaline earth metal ion and n=0 or 1, n being 0 when M is an alkaline earth metal ion, or (b) sodium glycin carbonate.

8. The pharmaceutical composition according to claim 1, wherein at least one of the polymers set forth in b) (i) and b) (ii) is an acidic polymer.

9. The pharmaceutical composition according to claim 1, wherein the single coating layer or the outermost coating layer contains an acidic compound.

10. The pharmaceutical composition according to claim 9, wherein the acidic compound is selected from the group consisting of citric acid, tartaric acid, fumaric acid, adipic acid, monosodium hydrogen citrate, monosodium tartrate, monosodium phosphate and mixtures thereof.

11. The pharmaceutical composition according to claim 1, wherein the active ingredient is selected from the group consisting of guaifenesine, prednisolone, dextromethorphan or a pharmaceutically acceptable salt thereof, a mixture of guaifenesine and dextromethorphan or a pharmaceutically acceptable salt thereof and a mixture of guaifenesine and phenylephrine or a pharmaceutically acceptable salt thereof.

12. The pharmaceutical composition according to claim 1, wherein the weight ratio between the polymer set forth in b) (i) and the carbon dioxide-releasing compound set forth in b) (iii) ranges from 10:1 to 1:5.

13. A medicament comprising a pharmaceutical composition according to claim 1 and at least one compound promoting salivation which is not a component of the pharmaceutical composition.

14. The medicament according to claim 13, wherein the compound promoting salivation is selected from the group consisting of sucrose, glucose, maltodextrin, sorbitol, mannitol, xylitol, maltitol, malbitol, inulin, isomalt and mixtures thereof.

15. The medicament according to claim 13, wherein the pharmaceutical composition according to claim 1 is present in admixture with the salivation-promoting compound.

16. A medicament package comprising a pharmaceutical composition according to claim 1, optionally at least one salivation-promoting compound and an instruction to administer the pharmaceutical composition and the salivation-promoting compound together.

17. The medicament of claim 13 formulated for direct oral administration into the mouth of a patient, wherein the medicament is adapted to be administered without first contacting the medicament with a liquid.

18. The medicament of claim 13 in the form of an aqueous dispersion suitable for drinking.

19. The pharmaceutical composition according to claim 1, wherein the weight ratio between the polymer set forth in b) (ii) and the polymer set forth in b) (i) ranges from 2:1 to 1:5.

* * * * *